(12) United States Patent
Burbank et al.

(10) Patent No.: US 6,427,081 B1
(45) Date of Patent: Jul. 30, 2002

(54) METHODS AND CHEMICAL PREPARATIONS FOR TIME-LIMITED MARKING OF BIOPSY SITES

(75) Inventors: Fred H. Burbank, San Juan Capistrano; Paul Lubock, Laguna Niguel; Michael L. Jones, Capistrano Beach; Nancy Forcier, Laguna Niguel, all of CA (US)

(73) Assignee: SenoRx, Inc., Aliso Viejo, CA (US)

( * ) Notice: Subject to any disclaimer, the term of this patent is extended or adjusted under 35 U.S.C. 154(b) by 0 days.

(21) Appl. No.: 09/654,920

(22) Filed: Sep. 5, 2000

Related U.S. Application Data

(63) Continuation of application No. 09/241,936, filed on Feb. 2, 1999.

(51) Int. Cl.⁷ .......................... A61B 19/00; A61B 8/08; A61B 8/12; A61B 10/00
(52) U.S. Cl. .................. 600/431; 600/420; 600/424; 600/458
(58) Field of Search ................. 600/414, 420, 600/426, 458; 424/9.1; 128/898, 899; 606/114, 117

(56) References Cited

U.S. PATENT DOCUMENTS

| | | |
|---|---|---|
| 3,818,894 A | 6/1974 | Wichterle et al. |
| 4,007,732 A | 2/1977 | Kvavle et al. |
| 4,331,654 A | 5/1982 | Morris |
| 4,545,367 A | 10/1985 | Tucci |
| 4,647,480 A | 3/1987 | Ahmed |
| 4,693,237 A * | 9/1987 | Hoffman et al. ............ 128/899 |
| 4,847,049 A | 7/1989 | Yamamoto |
| 4,909,250 A | 3/1990 | Smith |
| 5,221,269 A * | 6/1993 | Miller et al. ................ 604/281 |
| 5,236,410 A | 8/1993 | Granov et al. |
| 5,281,408 A | 1/1994 | Unger |
| 5,282,781 A | 2/1994 | Liprie |
| 5,334,381 A | 8/1994 | Unger |
| 5,422,730 A | 6/1995 | Barlow et al. |
| 5,494,030 A | 2/1996 | Swartz et al. |
| 5,549,560 A | 8/1996 | Van de Wijdeven |
| 5,636,255 A | 6/1997 | Ellis |
| 5,643,246 A | 7/1997 | Leeb et al. |
| 5,646,146 A | 7/1997 | Faarup et al. |
| 5,676,925 A | 10/1997 | Klaveness et al. |
| 5,688,490 A | 11/1997 | Tournier et al. |
| 5,902,310 A * | 5/1999 | Foerster et al. ............. 606/142 |
| 6,056,700 A * | 5/2000 | Burney et al. .............. 600/564 |
| 6,071,301 A * | 6/2000 | Cragg et al. ................ 606/213 |
| 6,161,034 A * | 12/2000 | Burbank et al. ............ 600/431 |
| 6,183,497 B1 * | 2/2001 | Sing et al. .................. 606/213 |

FOREIGN PATENT DOCUMENTS

| | | |
|---|---|---|
| EP | 146699 | 9/1984 |
| EP | 0481685 A1 | 10/1991 |
| WO | 93/14712 | 5/1993 |
| WO | 9314712 * | 8/1993 |
| WO | 96/08208 A1 | 3/1996 |
| WO | 9608208 * | 3/1996 |
| WO | 98/06346 | 2/1998 |
| WO | 9806346 * | 2/1998 |
| WO | 00 38579 A | 7/2000 |

* cited by examiner

*Primary Examiner*—Joseph Pelham
(74) *Attorney, Agent, or Firm*—Coudert Brothers LLP

(57) ABSTRACT

Detectable markers that may be introduced into a cavity created by removal of a biopsy specimen to mark the location of the biopsy site so that it may be located in a subsequent medical/surgical procedure. The markers remain present in sufficient quantity to permit detection and location of the biopsy site at a first time point (e.g., 2 weeks) after introduction but clear from the biopsy site or otherwise not interfere with imaging of tissues adjacent the biopsy site at a second time point (e.g., 5–7 months) after introduction.

36 Claims, 6 Drawing Sheets

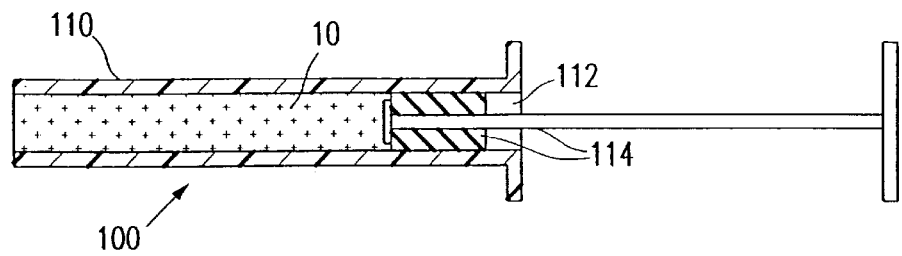
FIG. 4
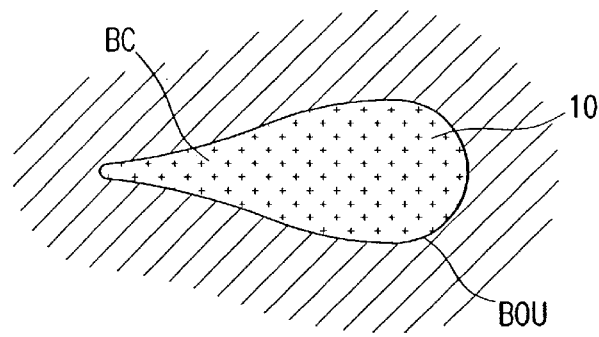
FIG. 5a
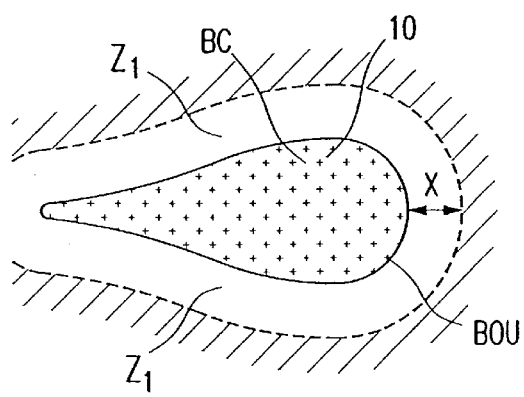
FIG. 5b
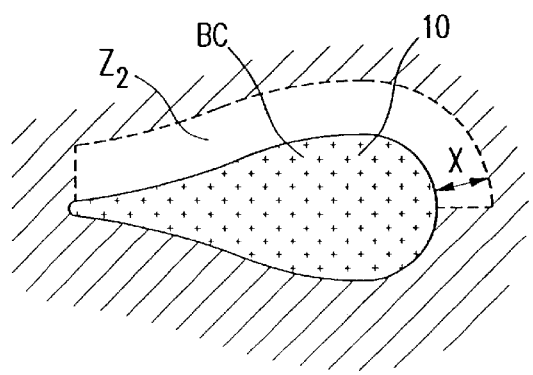

METHODS AND CHEMICAL PREPARATIONS FOR TIME-LIMITED MARKING OF BIOPSY SITES

This is a continuation application of copending application Ser. No. 09/241,936 filed Feb. 2, 1999, incorporated by reference.

FIELD OF THE INVENTION

The present invention pertains generally to the field of medicine and surgery, and more particularly to methods and compositions of matter which may be used to mark the location from which a tissue sample has been removed so that subsequent treatments (e.g., surgical excision, radiotherapy, drug therapy, etc.) may be precisely performed at such location.

BACKGROUND OF THE INVENTION

A. The use of Tissue Biopsies in Modern Medicine & Surgery

In modem medical practice small tissue samples, known as biopsy specimens, are often removed from tumors, lesions, organs, muscles and other tissues of the body. Such removal of tissue samples may be accomplished by open surgical technique (i.e., removal of a small sample of tissue through a small surgical incision using a local anesthetic), or through the use of a specialized biopsy instrument such as a biopsy needle. After the tissue samples have been removed, they are typically subjected to diagnostic tests or examinations such as a) gross and microscopic examination to determine cytology and/or histology, b) biochemical analyses to determine the presence or absence of chemical substances which indicate certain disease states, c) microbiological culturing to determine the presence of bacteria or other microbes, and/or d) other diagnostic procedures. The information obtained from these diagnostic tests and/or examinations can then be used to make or confirm diagnoses and/or to formulate treatment plans for the patient.

B. Special Considerations Relating to Biopsy of Breast Cancers

Approximately one in nine American women will develop breast cancer sometime in her life. Breast cancer is presently the most common cancer in women and is the second leading cause of cancer deaths in women. Periodic physical examination of the breasts is important for early detection of potentially cancerous lesions. Additionally, specialized X-ray studies known as mammography is a proven tool for diagnosing breast cancer in women over 40 years of age. Mammography is also believed by many medical practitioners to be diagnostically beneficial in younger women as well. In mammography, the breast is compressed between two plates while specialized x-ray images are taken.

If an abnormal mass in the breast is found by physical examination or mammography, ultrasound may be used to determine whether the mass is a solid tumor or a fluid filled cyst. Cystic lesions are generally benign and the diagnosis of a cystic lesion is often confirmed by needle aspiration of fluid from the interior of the cyst. (It should be noted, however, that the needle aspiration of cystic lesions is different from "needle biopsy" of solid masses as discussed herebelow). However, solid masses are usually subjected to some type of tissue biopsy to determine if the mass is cancerous.

If a solid mass or lesion is large enough to be palpable (i.e., felt by probing with the fingertips) a tissue specimen can be removed from the mass by a variety of techniques, including but not limited to open surgical biopsy or a technique known as Fine Needle Aspiration Biopsy (FNAB). In open surgical biopsy, an incision is made and a quantity of tissue is removed from the mass for subsequent histopathological examination. In the FNAB procedure, a small sample of cells is aspirated from the mass through a needle and the aspirated cells are then subjected to cytological examination.

If a solid mass of the breast is small and non-palpable (e.g., the type typically discovered through mammography), a relatively new biopsy procedure known as "stereotactic needle biopsy" may be used. In performing a stereotactic needle biopsy of a breast, the patient lies on a special biopsy table with her breast compressed between the plates of a mammography apparatus and two separate digital x-rays are taken from two slightly different points of view. A computer calculates the exact position of the lesion with X an Y coordinates as well as depth of the lesion within the breast. Thereafter, a mechanical stereotactic apparatus is programed with the coordinates and depth information calculated by the computer, and such apparatus is used to precisely advance the biopsy needle into the small lesion. Depending on the type of biopsy needle (s) used, this stereotactic technique may be used to obtain cytologic specimens (obtained through FNAB) and/or histologic specimens (obtained through coring needle biopsy). Usually at least five separate biopsy specimens are obtained from locations around the small lesion as well as one from the center of the lesion.

i. Potential Time Delay Between Biopsy and Commencement of Surgery or Other Treatment For some types of biopsies (other than those of breast lesions), "frozen sections" of the biopsy specimen may be prepared by a pathologist and such frozen sections may be used to arrive at a reasonably accurate diagnosis within minutes after removal of the biopsy specimen. Such frozen sections are prepared by rapid freezing of the tissue, slicing of the tissue into sections that are approximately greater than 10 microns thick and mounting of the section(s) on glass slides for immediate microscopic examination by a pathologist. Frozen sections of this type are not typically used for biopsies of breast lesions because the usual frozen section is too thick for definitive visualization and diagnosis of the cell types found in breast tumors. Instead, breast biopsy specimens are usually prepared for histopathological examination by a more traditional non-frozen technique wherein the tissue specimen is immersed in a chemical fixative solution (e.g., formalin, glutaraldehyde, etc.) For a period of time sufficient to cause crosslinking of the connective tissue proteins present in the tissue, the fixed tissue is sliced into thin sections approximately 8 microns thick, the tissue sections are mounted on and cell-selective histological stains are applied to stain the tissue prior to microscopic examination. This non-frozen tissue preparation technique typically requires at least 24–48 hours to complete and, as a result, the pathologist's diagnosis of the breast lesion may not be available until 24 to 72 hours after the biopsy specimen was removed from the breast. Thus, for these reasons, histopathological examination and diagnosis of breast lesions may be much more time consuming than the histopathological examination and diagnosis of other types of lesions. Thereafter, if a breast lesion has been diagnosed as cancerous, the patient may require some time (e.g., several days to more than a week) to consider each of the surgical options available to her, seek second opinion(s) and reach a treatment decision. The available surgical options for cancerous lesions of the breast include various degrees of mastectomy or lumpectomy. Moreover, in some cases, depending on the histology (type of cancer), grade (how aggressive it looks under the microscope), stage (how large the cancer is and how far it has spread), and additional prognostic or predictive information, the treating physicians may recommend that some radiation therapy or chemotherapy be performed before proceeding with surgical lumpectomy.

ii. Marking of Biopsy Sites to Facilitate Subsequent Location and Treatment of the Lesion In order for the surgeon or radiation oncologist to direct surgical or radiation treatment to the precise location of the breast lesion several days or weeks after the biopsy procedure was performed, it is desirable that a biopsy site marker be placed in or on the patients body to serve as a landmark for subsequent location of the lesion. Various types of biopsy site markers have been known in the prior art. For example, the prior art has included visually discernible markers that are applied externally to the patient's skin as described in U.S. Pat. Nos. 2,192,270 (Carswell, Jr.) and 5,147,307 (Gluck). Additionally, the prior art has included radiographically visible markers that may be introduced into the biopsy site such as marker wires that are inserted through the biopsy needle after a tissue sample is removed and are thereafter allowed to remain protruding from the patient's body and radiographically visible tissue markers (e.g., clips or staples) that are attached to tissue adjacent the site from which the biopsy specimen has been removed, as described in International Patent Publication No. WO 98/06346 (Biopsys Medical, Inc.). However, due to the consistency of breast tissue and the fact that these biopsy site markers are typically introduced while the breast is still compressed between the mammography plates, these biopsy markers of the prior art may become attached to adjacent bands of connective tissue that do not remain at the specific location of the biopsy after the breast has been decompressed and removed from the mammography apparatus. Furthermore, at least some of the biopsy site markers of the prior art can remain present at the site of implantation for an indefinite period of time if not surgically removed. Thus, if surgery is deemed not to be presently indicated (or if the patient elects not to have surgery performed), the prior art radiographic biopsy site markers can remain intact indefinitely and may obscure or interfere with follow-up or subsequent mammography or imaging studies. Although International Patent Publication No. WO 98/06346 does mention that the clip-type tissue markers disclosed therein may be "biodegradable" such publication provides no information as to what materials could be used to form such a "biodegradable" tissue marker or the preferred time period in which the tissue marker is to remain present (i.e., non-degraded and visible) at the biopsy site.

Thus, there remains a need in the art for the development of biopsy site markers that a) are deliverable into the cavity created by removal of the biopsy specimen (and not into tissue that is located outside of that biopsy cavity), b) will not migrate from the biopsy cavity even when the breast tissue is moved, manipulated or decompressed, c) will remain detectable at the biopsy site (e.g., within the biopsy cavity or at the site where the biopsy cavity once existed) until at least a predetermined first time point (e.g., 2 weeks after the biopsy) to facilitate subsequent location of the biopsy site by a surgeon or radiation oncologist and d) will clear sufficiently from the biopsy site or otherwise not interfere with imaging of the biopsy site and adjacent tissues at a second predetermined time point (e.g., 6 months after the biopsy) so as not to obscure or interfere with follow-up mammography or imaging procedures.

SUMMARY OF THE INVENTION

The present invention provides chemical preparations and methods for marking biopsy sites, whereby a detectable marker (i.e., a substance or article that is detectable by imaging and/or palpation and/or visualization) is introduced into the cavity created by removal of a biopsy specimen (e.g., the "biopsy cavity") such that (i) the marker will remain present and detectable at the biopsy at a first time point (e.g. 2 weeks after introduction), and (ii) the marker will clear sufficiently from the biopsy site, or will otherwise be undetectable by imaging so as not to interfere with follow-up imaging of the biopsy site and adjacent tissues at a second time point (e.g. typically 5–8 months and preferably at about 6 months after introduction).

A. Types of Markers (i) Imageable Embodiments of the Marker

In embodiments of the invention wherein the marker is detectable by imaging, it will typically be imageable by a suitable imaging means or apparatus. For example, the marker may be radiographically visible (e.g., more radiopaque or more radiolucent than the surrounding tissue so as to be imageable by x-ray, CT scan, mammography, fluoroscopy, or other roentgenological means. In other imageable embodiments, the marker may be imageable by other means such as magnetic resonance imaging (MRI), ultrasound, Doppler, or other presently known or hereafter invented imaging techniques.

(ii) Palpable Embodiments of the Marker

In embodiments of the invention wherein the marker is detectable by palpation, the marker will comprise a space occupying substance or object(s) that, when introduced into the cavity created by the removal of the biopsy specimen, will form a palpable mass that can be located by closed palpation of the breast and/or by local palpation by a surgeon during dissection of the surrounding breast tissue. Space occupying markers that are palpable include balloon(s), beads, microspheres, of flowable bulking materials such as collagen.

(iii) Visually Discernible Embodiments of the Marker

In embodiments of the invention wherein the marker is visually detectable, the marker will comprise a substance or object(s) that is of a color that is different from the color of breast tissue and blood such that, when introduced into the cavity created by the removal of the biopsy specimen, the marker will be visually detectable by a surgeon during dissection of the surrounding breast tissue.

(iv) Energy-Emitting Embodiments of the Marker

In some embodiments of the invention, the marker may emit energy that is detectable by a suitable detection apparatus. For example, the marker may comprise a radioactive substance that is detectable by way of a gamma detector, scintillation counter or other apparatus for detecting radiation. Similarly, the marker may comprise a signal emitting apparatus (e.g. a transmitter or transponder) that will continuously, or occasionally when interrogated by ultrasound or other type of interrogating energy, emit a signal (e.g., radiofrequency, ultrasound, etc.) that can be detected by an apparatus that is useable to detect that particular type of signal.

(v) Embodiments of the Marker That are Detectable by More Than One Detection Means In some embodiments of the invention, the detectable marker may be detectable by a combination of any two or more of the above-summarized imaging, visual, palpation and/or emission/detection techniques. For example, an imageable marker of the present invention may additionally comprise a palpable component as described above (e.g., a space occupying material or article) so as to render the marker both imageable and palpable after implantation at the biopsy site. Alternatively, an imageable marker of the present invention may additionally be provided with a visible component as described above (e.g., a colored substance or article) so as to render the marker both imageable and visually discernible after implantation at the biopsy site similarly, by way of illustrative example, an imageable marker of the present invention may additionally comprise a palpable component as described above (e.g., a space occupying material or article) and a visible component as described above (e.g., a colored substance or article) so as to render the marker imageable, palpable and visible during surgery.

B. Consistency and Properties of the Marker
(i) Substantially Insoluble Marker Substances In accordance with the invention, the detectable marker may comprise a substance (e.g., a gas, lipid, oil, powder, suspension or slurry) that may be delivered into the cavity formed by removal of a biopsy sample (i.e., the "biopsy cavity"), and which has solubility and/or biodistributive properties that allow it to remain present and detectable (e.g., imageable, palpable, energy-emitting and/or visible) at the biopsy site until at least the first predetermined time point (e.g., at least 2 weeks after introduction), but which will allow the substance to be substantially cleared (e.g., dissolved, distributed from or locally metabolized) from the biopsy site at the second predetermined time point (e.g., 6 weeks after introduction).

(ii) Soluble Marker Substances That are Combined with Clearance Delaying Element(s)

Further in accordance with the invention, the detectable marker may comprise a) a detectable (e.g., imageable, palpable, energy-emitting and/or visible) substance that, if delivered alone into the cavity formed by removal of the biopsy specimen, would clear from such biopsy cavity so as to be no longer detectable at the first predetermined time point (e.g., two (2) weeks after introduction) in combination with b) a clearance limiting element (e.g., a diffusion-limiting polymer matrix, a membrane or liposomal encapsulation, a biodegradable matrix or encapsulant, etc . . . ) that will limit the dissolution, biodistribution and/or local metabolism of the detectable substance to remain present and detectable at the biopsy site for at least 2 weeks after introduction, but which will allow the detectable substance to be substantially cleared (e.g., dissolved, distributed from or locally metabolized) from the biopsy site at the second predetermined time point (e.g., 5–8 months and preferably at about 6 months after introduction).

(iii) Markers That Remain Present at the Biopsy Site Without Interfering with Subsequent Follow-Up Imaging Studies Still further in accordance with the invention, the detectable marker may comprise a substance or article that is detectable by a detection method that is different from the imaging method that is intended to be used for follow-up imaging of the biopsy site and adjacent tissues, thus allowing the marker to reside at the biopsy site beyond the second time point (i.e., that time point at which follow-up imaging studies are to be conducted) or even indefinitely, without interfering with such follow-up imaging studies. For example, the marker may be detectable by palpation, visualization and/or ultrasound but not visible on x-ray, thereby allowing for follow-up x-ray studies without interference by the marker while remaining locatable by palpation, visualization, specialized detection and/or ultrasound in the event that a surgeon, radiologist or other practitioner may wish to subsequently locate the biopsy site.

(iv) Markers That Adhere to the Wall(s) of the Biopsy Cavity

Still further in accordance with the invention, the detectable marker of the present invention may comprise, or may be combined with, an adhesive which will cause the detectable marker to adhere to tissue immediately adjacent the void created by removal of the biopsy sample.

C. Methods for Surgical Excision Using Biopsy Site Markers of the Present Invention Still further in accordance with the invention, there are provided methods for surgical excision of tissue that is located adjacent to or surrounding a biopsy cavity in which a visually detectable marker of the present invention has been delivered. The method generally comprises the steps of a) visualizing the perimeter of the visually discernible marker and b) excising tissue that lies adjacent to the perimeter of said visually discernible marker. This method of surgical excision may be used to accurately excise and remove a quantity of tissue of a specific width (e.g., a region or band that is 2 centimeters wide) that surrounds or lies adjacent to the original biopsy cavity. Because the biopsy site markers of the present invention actually occupy the original biopsy cavity, they serve to accurately mark the perimeter of that biopsy cavity. As such, the surgeon is able to accurately visualize the boundary of the biopsy cavity and to then excise and remove tissue that lies within a certain distance (e.g., 2 centimeters) of that cavity boundary. Such visualization of the biopsy cavity boundary may be made easier or enhanced when the biopsy site marker comprises, in addition to a visually discernible component such as a dye or carbon particles, a space-occupying bulking agent as described above in reference to palpable embodiments of the invention as the presence of such space occupying or bulking agent may serve to dilate or distend the biopsy cavity, thereby making it easier for the surgeon to visualize the boundaries of that biopsy cavity. This surgical excision method may be particularly suitable in cases where the histopathological evaluation of the biopsy specimen suggests that additional cancerous cells may continue to reside in tissue located within a certain distance of the original biopsy cavity boundary.

Additional objects, embodiments and advantages of the present invention will become apparent to those of skill in the relevant art upon reading and understanding of the following detailed description of preferred embodiments and the accompanying drawings.

BRIEF DESCRIPTION OF THE DRAWINGS

FIG. 4 is a longitudinal sectional view of an injector device that is useable to introduce a solid (e.g., powdered, particulate or granular) marker substance of the present invention into a biopsy site.

FIGS. 5a–5c are showings of a preferred method of excising and removing tissue that lies within a predetermined zone located on all sides or only one side of the boundary of a previously-created biopsy cavity.

DETAILED DESCRIPTION OF THE PREFERRED EMBODIMENTS

The following detailed description, and the accompanying drawings to which it refers are provided for purposes of exemplifying and illustrating representative examples and embodiments of the invention only, and are not intended to limit the scope of the invention in any way. Indeed, no effort has been made to exhaustively illustrate and describe all possible embodiment and configurations in which the present invention may take physical form.

Figures 1, 1A:
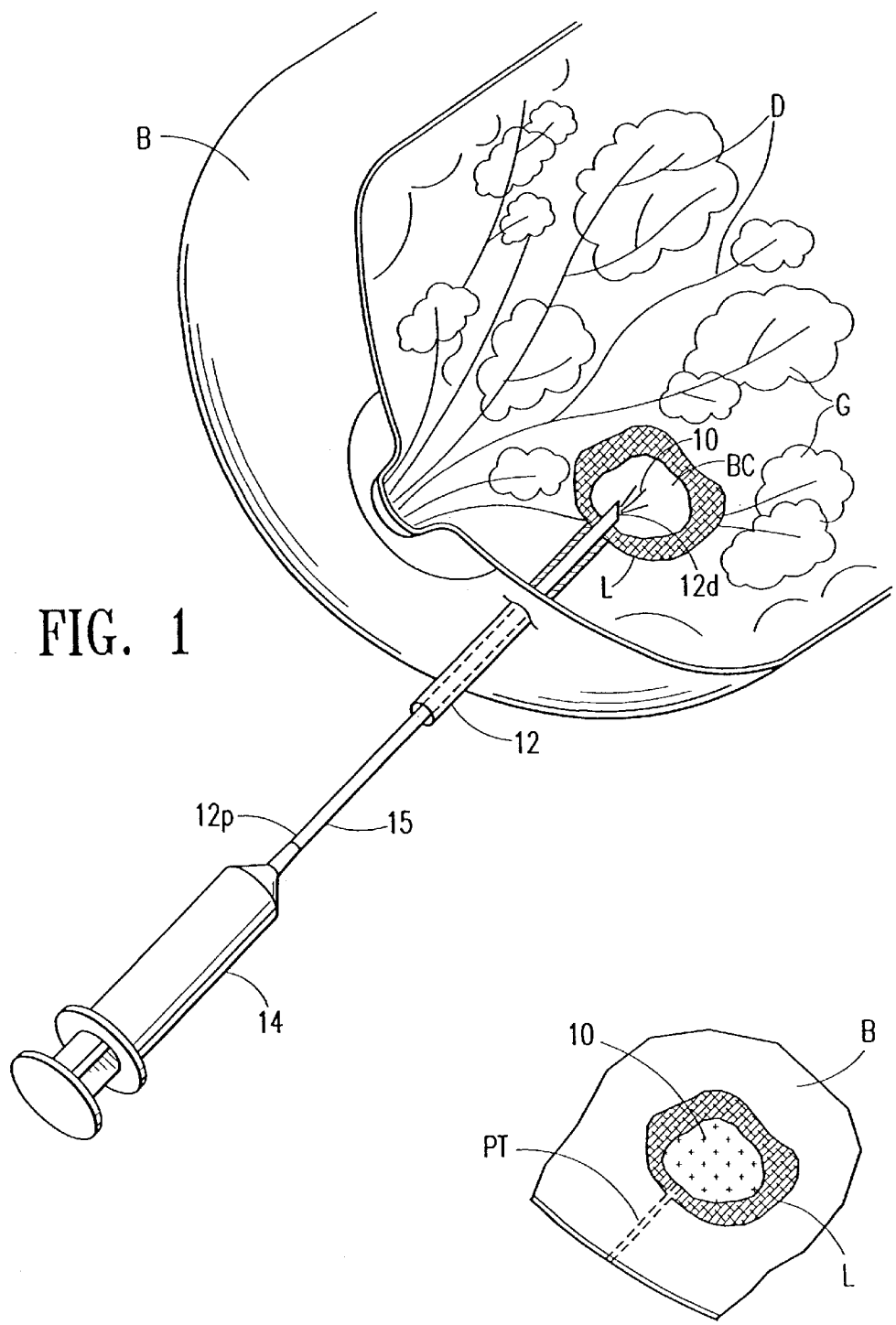
FIG. 1 is a perspective view of a human breast having a lesion from which a biopsy specimen has been removed, and showing a syringe and introduction cannula operatively positioned for introduction of an detectable marker of the present invention into the cavity created by removal of the biopsy specimen.
FIG. 1a is an enlarged perspective view of a portion of the breast of FIG. 1 after the detectable marker has been introduced and after the syringe and introduction cannulas have been removed.
Figure 2A:
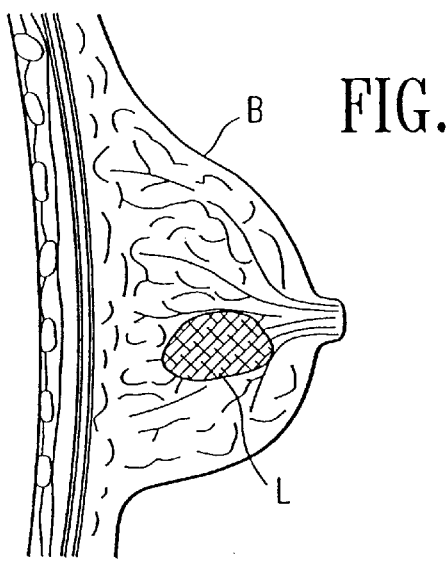
FIGS. 2a–2g are schematic, step-by-step showings of a preferred method for using an detectable marker of the present invention to mark the site of a lesion that has been biopsied while the breast is compressed within a mammography apparatus.
Figure 2B:
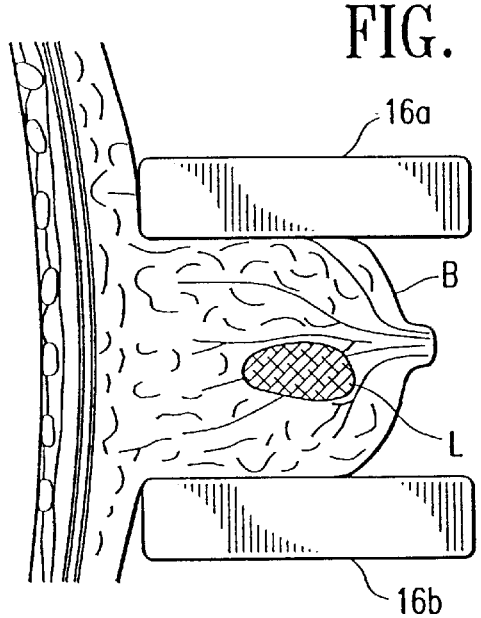
Figure 2C:
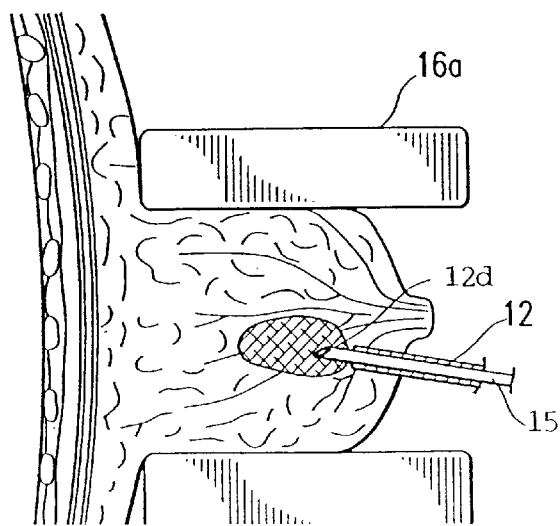
Figure 2D:
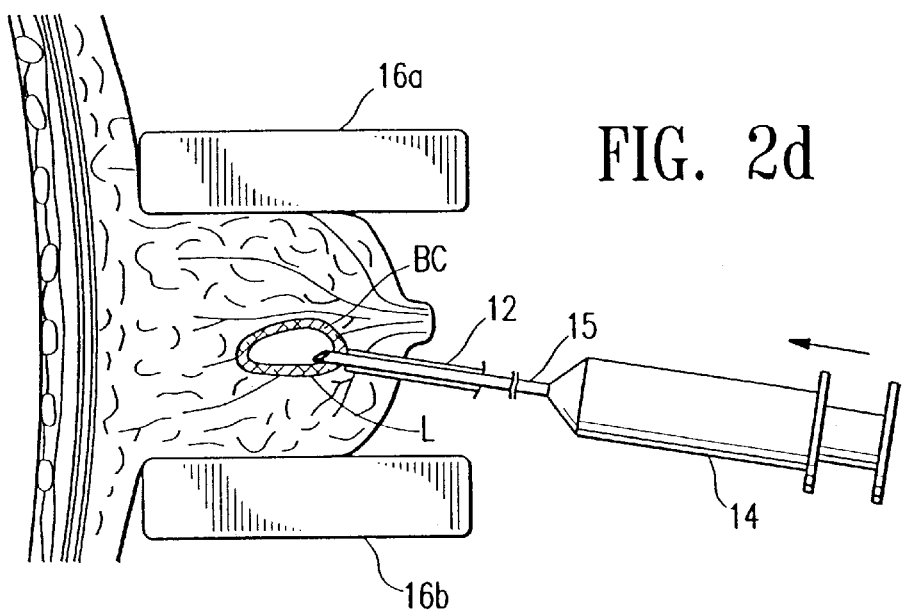
Figure 2E:
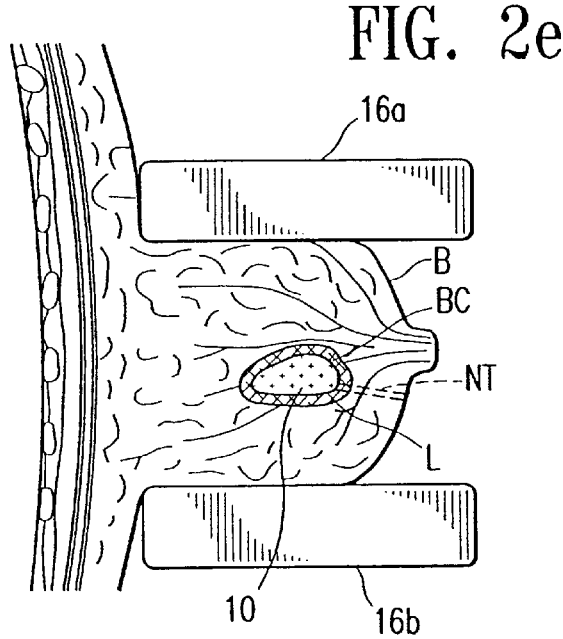
Figure 2F:
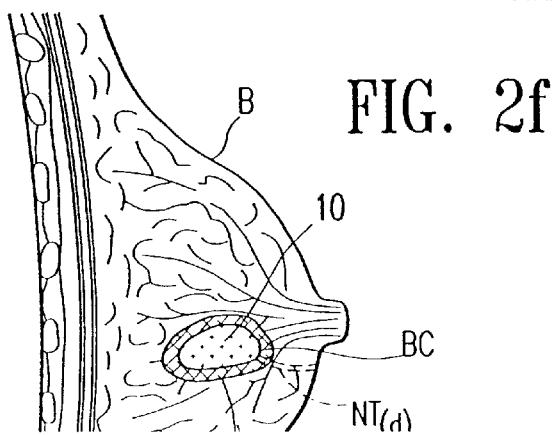
Figure 2G:
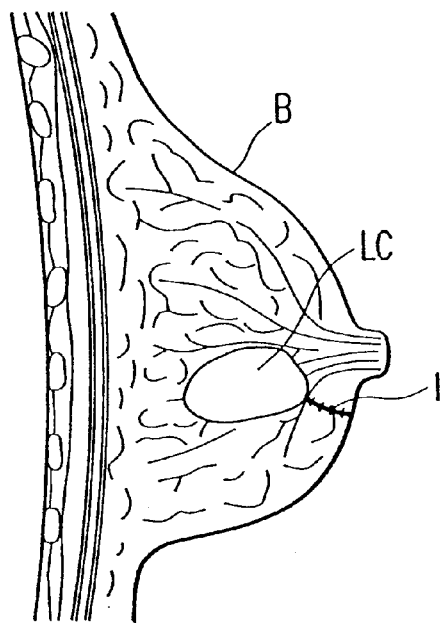
Figure 2G:
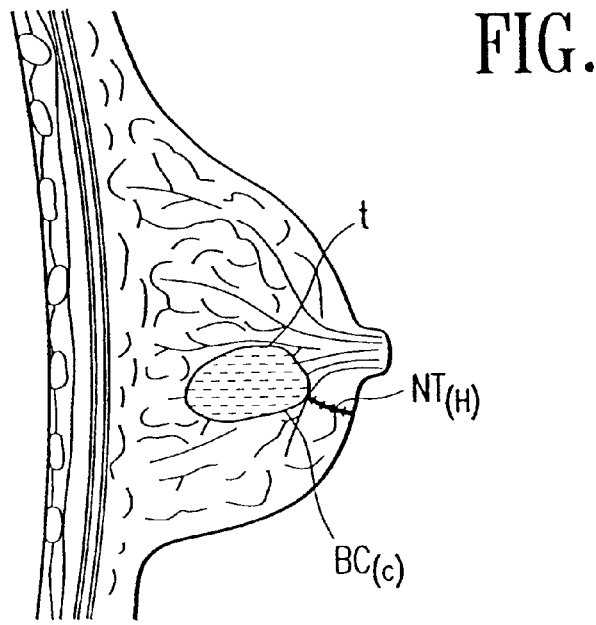

FIGS. 1 and 1a shows a human breast B which contains a lesion L, such as a mass suspected to be cancerous. An outer cannula 12 has been inserted percutaneously into the lesion L and a biopsy needle (not shown) has been passed through the outer cannula 12 and used to remove a biopsy specimen from the center of the lesion, thereby forming a biopsy cavity BC within the lesion L. After removal of the biopsy needle (not shown), a marker introduction cannula 15 has been passed through the outer cannula such that its distal end 12d is located within the biopsy cavity BC. A device 14 for delivering a flowable, detectable marker 10 of the present invention is attached to the proximal end 12p of the introduction cannula 15 and is being used to inject a quantity of the detectable marker 10 into the biopsy cavity BC, as shown.

FIGS. 2a–2g' are schematic, step by step showings of a preferred method for using a detectable marker 10 to mark the site of a lesion L that has been biopsied while the breast B is compressed within a mammography apparatus 16a and 16b.

A. Properties and Functional Requirements of the Detectable Marker i. Preferred Imageable and Instrument-Detectable Embodiments The detectable markers 10 of the present invention may be visible on an image created by the particular type or imaging device(s) available during the procedure. In many cases, a form of roentgenographic imaging (e.g., mammography, x-ray, fluoroscopy, CT, etc.) will be used, and the imageable marker 10 will thus comprise a material that is more or less radio- lucent or more or less radiopaque than the tissue surrounding the biopsy cavity (e.g., air, other gas, lipid, oil, a metal salt, barium powder, etc.) such that the marker 10 can be imaged by such x-ray means. In other instances, ultrasound imaging may be used and the imageable marker will comprise a material or substance that has different ultrasound reflective properties (and possible different radiographic density) than the body tissue surrounding the biopsy cavity BC (e.g., air, carbon dioxide, other gasses, saline solution, other liquids, etc.) In other instances, a magnetic imaging technique such as magnetic resonance imaging (MRI) may be used and the imageable marker 10 will comprise a ferromagnetic material or material (e.g., iron powder) having different magnetic density than the body tissue surrounding the biopsy cavity BC.

Similarly, the marker 10 may be a substance or article that emits energy (e.g., radiation) that is detectable by an instrument (e.g., a gamma detector).

ii. Preferred Palpable Embodiments

The preferred palpable embodiments of the invention comprise a substance (e.g., a collagen material as described in U.S. Pat. No. 4,066,083) or an article balloon(s), bead(s), etc.) that are sufficient mass to be palpated and located by tactile means while disposed within the biopsy site.

iii. Preferred Visible Embodiments

The preferred visible embodiments of the invention may comprise a colored substance such as a dye or colorant (e.g., methylene blue, gentian violet, indigo, dyes used in tattooing, etc.) or colorant particles (e.g., india, indigo, carbon particles or carbon preparations described in Langlois, S. L. P. and Carter, M. L., Carbon Localization of Impalpable Mammographic Abnormalities, Australas Radiol. 35: 237–241 (1991) and/or Svane, G. A Stereotaxis Technique for Preoperative Marking of Non-Palpable Breast Lesions, Acta Radiol. 24(2): 145–151 (1983).

iv. Preferred Combination Embodiments

The markers 10 of this invention may combine the attributes of any of the imageable, palpable and/or visible embodiments to provide for detection of the marker 10 by multiple means, such as a) imaging and palpation, b) imaging and visualization, c) imaging, palpation and visualization, or d) visualization and palpation.

a. Example of Radiographically Visible/Palpable Marker Material Formed of Metal tons In Combination With a Collagenous or Gelatinous Matrix U.S. Pat. No. 4,847,049 (Yamamoto) describes an ion-impregnation or chelation technique whereby an ion may be impregnated or chelated to collagen for the purpose of imparting antimicrobial properties to the collagen preparation. Thus, using this technique, imageable ions such as radiographically visible metal ions, may be bound to a bulky collagenous material to form a marker 10 that may be a) imaged by radiographic means and b) located by palpation of tissue surrounding the biopsy site. For example, a silver ion-renatured collagen composition may be prepared by the following process:

Step 1-Renaturation of Collagen (or Gelatin):

Collagen may be renatured to an insoluble form by processing denatured collagen that has been obtained from a natural source such as bovine corium (hide), bovine tendon, and porcine skin. Alternatively, pre-processed, insoluble collagen may be purchased in the form of a commercially available hemostatic material such as Colla™ and Avitene™ nonwoven web. Methods for renaturing collagen are known in the literature, including, for example, those methods described in U.S. Pat. Nos. 4,294,241 and 3,823,212.

A particularly preferred form of renatured collagen for utilization in accordance with the present invention is one that has been renatured and covalently cross-linked. This collagen may be prepared by utilizing readily available polyfunctional cross linking agents or fixatives, such as dialdehydes, dicarboxylic acids, diamines, and the like. Typically, tropocollagen is dissolved in a buffer of pH 3.0 to 5.0 to provide a solution containing approximately 1 to 2% by weight of the collagen. Then 1% of a dialdehyde cross-linking agent such as glutaraldehyde or formaldehyde is then added. The mixture is then frozen and stored for approximately 24 hours. After thawing and washing to remove unreacted cross linking agent, the renatured cross-linked collagen is then ready for contact with a silver ion-containing solution.

Step 2-Binding of Metal Ions to the Renatured Collagen:

The source of silver ion may be a water soluble silver salt, preferably silver nitrate. While the concentration of the silver ion in the solution is not particularly critical, it will be usually convenient to utilize solutions in the concentration range of about 10 to $10^3$ millimolar.

The renatured collagen is preferably contacted with a silver ion-containing solution in the pH range of about 4 to 9. The pH of the silver ion-containing solution can be controlled by the addition of an appropriate titrating agent, such as nitric acid, or potassium hydroxide, as required, to maintain the pH at less than about 9.0 to avoid the degradation of the silver. There is not believed to be any lower limit for the pH, however, normally a pH above 4.0 will be convenient. A particularly preferred range for the pH is from 7.0 to 7.5. The binding capacity of silver by collagen is particularly effective within this preferred pH range, although the amount of binding by silver by the collagen is further controllable by the concentration of the silver ion-containing solution and/or exposure time of the collagen to the silver ion-containing solution. Simultaneous with or subsequent to exposure of the collagen to the silver ion-containing solution, the collagen is then exposed to ultraviolet radiation of energy and duration sufficient to strengthen the binding of the silver ions to the collagen without substantial formation of metallic silver formed as a result of oxidation of various functional groups in the collagen by the silver ion. While the exact limits of the ranges of the conditions which will be sufficient to strengthen the binding of the silver ions without substantial formation of metallic silver are not precisely determinable, it will generally suffice to maintain the pH of the silver-collagen environment at less than 8.0 while exposing the collagen to ultraviolet radiation in the range of about 210 to 310 nm wavelength for about from 5 to 15 minutes. The time of UV exposure for complete reaction is inversely proportional to the light intensity which is preferably in the range of 100 to 1,000 microwatts/cm. A slight coloration of the collagen due to the exposure to ultraviolet radiation is acceptable, i.e., a turning from white to a light brown to yellow color, indicating a slight oxidation reaction occurring in the collagen, however, the radiation should not be to the extent that dark brown or black areas in the collagen occur due to over-oxidation and/or substantial formation of metallic silver. Normally the exposure will be performed at ambient temperatures, i.e., in the range of about 20 degrees to 25 degrees C, however, there is not believed to be any reason why the exposure could not occur at higher or lower temperatures providing that the temperature is not high enough to cause degradation of the collagen and/or silver ion. There is not believed to be any lower limit to the temperature at which the exposure may take place, provided it is above the freezing point of the ion-containing solution.

Ultraviolet radiation may be provided by any conventional ultraviolet radiation source of appropriate wavelength, such as germicidal lamps and mercury/xenon lamps.

Step 3 (optional)-Addition of Visible Marker Component to the Collagen or Gelatin Matrix:

If it is desired for the marker to be detectable visually, as well as by imaging and palpation, a quantity of a visible substance having a color dissimilar to blood or tissue may be added. For example, carbon particles or a dye (e.g., methylene blue, indigo) may be added to the above-prepared silver ion/collagen preparation to provide a colored silver ion/collagen marker 10 that is imageable (by radiographic means), palpable (by hand) and visible (under white light in the operating room).

The above-described collagen-metal ion marker 10 (with or without visible marker component) is introduced into the cavity created by removal of the biopsy specimen. The quantity of this marker 10 introduced may be sufficient to distend or stretch the biopsy cavity somewhat, thereby creating a more palpable and obvious mass of marker material at the biopsy site.

Renatured gelatin or a cross-linked gelatin preparation such as Gelfoam™ may be impregnated or combined with a metal ion to provide a gelatin-metal ion marker material. The gelatin may be prepared and ion-bound by the same method as set forth hereabove for collagen.

a. Example of Radiographically or Ultrasonically Visible/Palpable Marker Material Formed of a Gas in Combination With a Collagenous or Gelatinous Matrix Step 1-Renaturation of Collagen (or Gelatin):

Collagen or gelatin is renatured, as by the method described in Step 1 of the immediately preceding example and described in the literature, including, for example, those methods described in U.S. Pat. Nos. 4,294,241 and 3,823,212.

Step 2-Dispersing of Air or Other Gas in the Renatured Collagen or Gelatin Matrix Air or another biologically inert gas (e.g., carbon dioxide) is then dispersed throughout the renatured collagen or gelatin matrix by a suitable means such as mixing, mechanical blending, nucleation, bubbling, etc. This results in the formation of many small gas bubbles throughout the collagenous or gelatinous matrix and provides a marker substance 10 that can be introduced into the biopsy cavity through a cannula or tube and is substantially more radio-lucent than the tissue surrounding the biopsy cavity. In this regard, this marker 10 can be imaged by x-ray or ultrasound but will not block or obscure imaging of tissue that lies immediately adjacent the biopsy cavity. Also, because of the bulk of the collagen or gelatin matrix, this marker 10 is readily palpable and locatable by tactile means within the surrounding breast tissue or other tissue.

Step 3 (optional)-Addition of Visible Marker Component:

If it is desired for the marker to be detectable visually, as well as by imaging and palpation, a quantity of a visible substance having a color dissimilar to blood or tissue may be added. For example, carbon particles or a dye (e.g., methylene blue, indigo) may be added to the above-prepared silver -ion/collagen preparation to provide a colored silver ion/collagen marker 10 that is imageable (by radiographic means), palpable (by hand) and visible (under white light in the operating room).

In routine use, the above-described collagen/gas or gelatin/gas marker 10 (with or without visible marker component) is introduced into the cavity created by removal of the biopsy specimen. The quantity of this marker 10 introduced may be sufficient to distend or stretch the biopsy cavity somewhat, thereby creating a more palpable and obvious mass of marker material at the biopsy site.

v. Preferred Residence Time of the Marker at the Biopsy Site

The detectable markers 10 of the present invention are formulated and/or constructed so as not to move or migrate from the biopsy site when the surrounding tissue is flexed or reconfigured (e.g., as occurs when a breast is decompressed and removed from a mammography machine). Additionally, the detectable markers 10 are formulated and/or constructed to (i) remain present at the site in sufficient quantity to permit imaging and location of the site for at least two (2) weeks after introduction and (ii) clear sufficiently from the site to permit imaging of tissue adjacent to the site, without interference from said detectable marker, at six (6) months after introduction.

Because the marker 10 is located at, and does not move or migrate from, the biopsy site it serves as a landmark that the surgeon may use to locate and treat or remove the remaining portion of the lesion without having to dissect and explore the surrounding tissue in attempting to locate the lesion. This aspect of the invention is particularly beneficial in cases (such as breast lumpectomy procedures) where it is desired to surgically remove the lesion L with minimal disfigurement, scarring or change in architecture of the surrounding tissue.

Because the marker 10 remains detectable at the biopsy site for at least two (2) weeks, the commencement of medical or surgical treatment of the lesion L may be delayed for up to two (2) weeks following the removal of the biopsy specimen and the marker 10 will still be present and useable to assist the treating surgeon or other physician in locating and directing treatment to the remaining portion of the lesion. This two (2) week minimum period of residence is especially beneficial in cases where immediate frozen sections can not be read by a pathologist, such as cases of suspected breast cancer wherein a small, non-palpable lesion of the breast has been biopsied by stereotactic biopsy, and the biopsy specimen is sent for routine histopathological evaluation (e.g., fixing, staining and microscopic examination) which takes several days to complete.

Also, because the marker substantially clears from the biopsy site within six (6) months after its introduction, it will not interfere with or obscure subsequent diagnostic imaging of any remaining portion of the lesion L or the surrounding tissue. This six (6) month maximum residence time of the marker is especially beneficial in cases where the lesion is determined not to be cancerous at present, but presents a risk for future tumorigenesis that warrants periodic imaging of the site of the lesion L and surrounding tissue.

a. Embodiments Where the Properties of The Marker's Detectable Component Alone Result in Desired Residence Time In some embodiments, the detectable marker 10 may comprise a detectable material that has pharmacokinetic properties (e.g., solubility, dissolution, potential for distribution from the biopsy site, potential for local metabolism or break down at the biopsy site) that cause it to remain present at the biopsy site in sufficient quantity to permit imaging of and location of the site for at least 2 weeks after its introduction, while clearing sufficiently from the site to permit imaging of tissue adjacent to the site without interference from said detectable marker, at 6 months after introduction.

In many applications of the invention, the particular pharmacokinetic or biodistributive property(ies) that determine the rate at which the marker 10 clears from the biopsy site may include its solubility in the interstitial fluids that are present at the biopsy site. In this regard, it has been determined that when the marker 10 is formed of detectable material having a solubility coefficient of less than $1 \times 10^{-3}$ grams per 100 cubic centimeters of water, such detectable material will typically have the desired detectable residence time within the biopsy site of at least two (2) weeks but not more than 5 to 7 months, and preferably not more than about 6 months. However, it will be appreciated that the detectable residence time of the marker 10 at the biopsy site will additionally vary with the amount of marker 10 material that has been introduced in the biopsy cavity. In this regard, a large volume of a material having a relatively high solubility coefficient can be introduced into the biopsy cavity to ensure that, even though the material hag a relatively fast clearance rate, an imageable amount of the material will remain present at the biopsy site at the first time point (e.g., two (2) weeks). On the other hand, a relatively small volume of material having a low solubility coefficient may be introduced into the biopsy cavity and, due to its slow clearance rate, will remain imageable at the biopsy site at the first time period (e.g., two (2) weeks).

Specific examples of radiographically visible materials that, if introduced into the biopsy site alone, would exhibit the desired detectable residence time (i.e., at least 2 weeks but not more than 6 weeks) include but are not necessarily limited to; AgCl; AgI; $BaCO_3$; $BaSO_4$; K; $CaCO_3$; ZnO; $Al_2O_3$; and the possible combinations thereof.

b. Embodiments Where the Properties of the Marker's Detectable Component Would Cause it to Clear From the Biopsy Site Too Rapidly But Wherein The Detectable Component Is Combined With a Clearance Delaying Element to Provide the Desired Residence Time In other embodiments, the detectable marker 10 may comprise detectable material that, if introduced into biopsy site alone, would clear substantially from the biopsy site in less than two (2) weeks after its introduction, thereby failing to provide the desired minimum detectable residence time at the biopsy site of at least two (2) weeks. In such embodiments, the detectable material will be combined (e.g., mixed with, encapsulated by, suspended in, etc.) a clearance delaying element that will cause the detectable material to remain present at the biopsy site in sufficient quantity to permit imaging of and location of the site for at least 2 weeks after its introduction, while still allowing the detectable material to clear sufficiently from the biopsy site to permit imaging of tissue adjacent to the site without interference from said detectable marker, at 6 weeks after introduction.

Examples of radiographically visible materials that would clear from most biopsy sites in less than two (2) weeks include but are not necessarily limited to; air, gas, lipid, oil, $AgNO_3$; ammonium salts; sodium salts; potassium salts; ethiodized oil (Ethiodol available commercially from Savage Laboratories, Mellville, N.Y., and certain radiographic contrast agents such as iohexol (Omnipaque, available from Nyegaard-Schering AG, available from Squibb/Bristol Myers.

Examples of clearance delaying elements that may be combined with the detectable material to form a detectable marker of the present invention include but are not necessarily limited to; polylactic acid; polyglycolic acid; polycapriolactone; an encapsulating membrane surrounding the detectable material.

The following examples are presently preferred formulations for detectable markers 10 of this embodiment:

| Component | Amount |
|---|---|
| Formulation 1 | |
| AgNo$_3$ | 20–70 parts by weight |
| Polylactic Acid | 30–80 parts by weight |
| Formulation 2 | |
| Ethiodol | 10–50 parts by weight |
| Polyglycolic Acid | 50–90 parts by weight |
| Formulation 3 | |
| Ethiodol | 10–70 parts by weight |
| Topical Thrombin | 30–90 parts by weight |
| Formulation 3 | |
| Polylactic Acid | 50–70 parts by weight |
| Air | 30–50 parts by weight | vi. Form and Consistency of the Detectable Marker

Figure 3A:
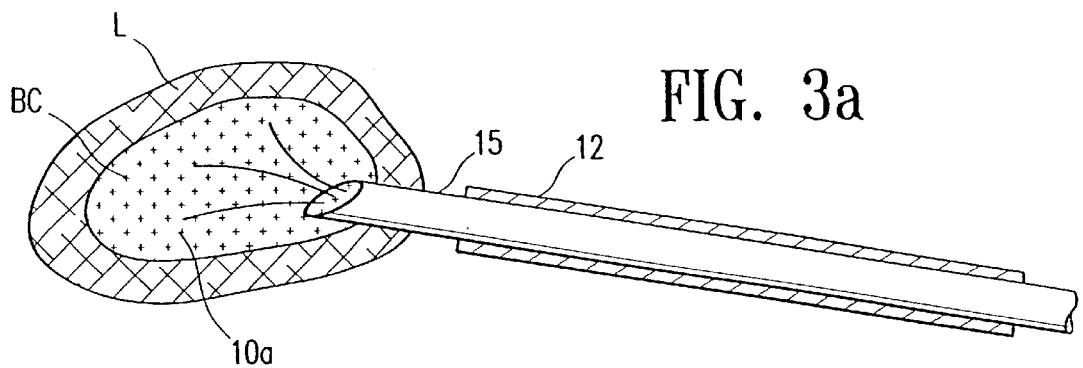
FIG. 3a is a schematic showing of a first embodiment of an detectable marker of the present invention after introduction into a biopsy site.
Figure 3B:
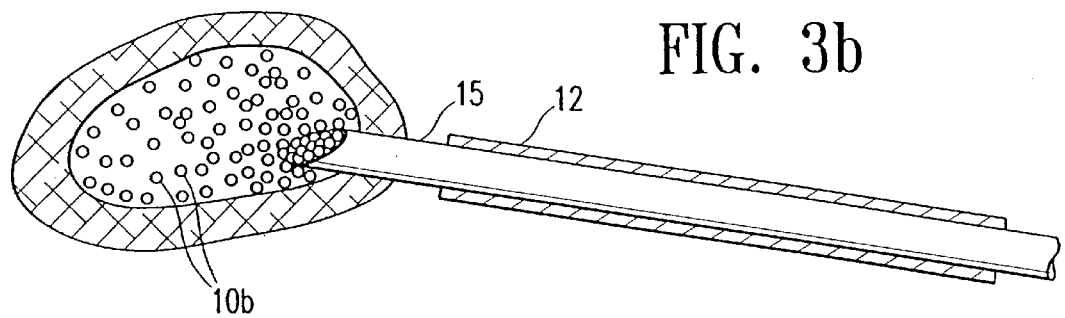
FIG. 3b is a schematic showing of a second embodiment of an detectable marker of the present invention after introduction into a biopsy site.
Figure 3C:
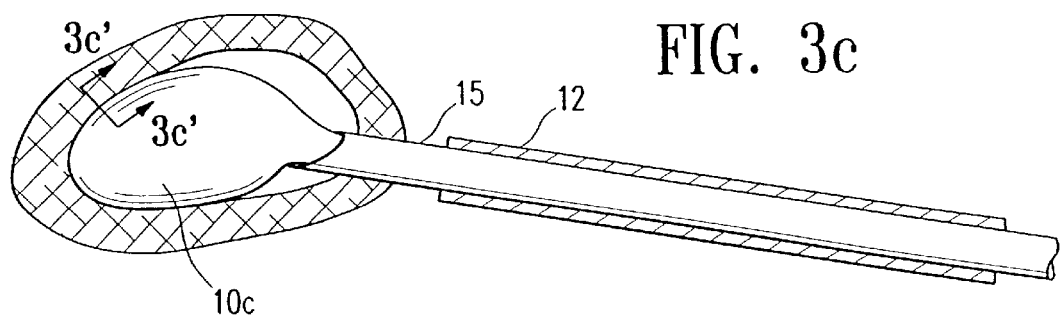
FIG. 3c is a schematic showing of a third embodiment of an detectable marker of the present invention after introduction into a biopsy site.
Figure 3C:
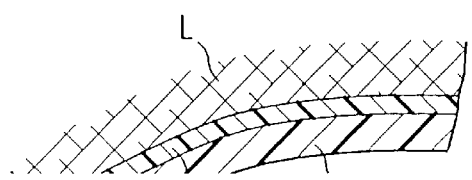

FIGS. 3a–3c illustrate examples of the different possible forms or consistencies of detectable markers 10 of the present invention.

a. Flowable Markers

FIG. 3a shows an example of a detectable marker 10a of a flowable consistency that is injectable through the lumen of the introduction cannula 15 into the biopsy cavity BC formed within the lesion L. Typically, such flowable markers 10a will comprise a dry powder, suspension, or solution. For example, a quantity of dry AgCl powder of 10–1000 micron particle size may be passed through the introduction cannula 15.

FIG. 4 shows an example of an injector device 100 that is useable in place of the introduction cannula 15, to introduce a solid (e.g., powdered, particulate or granular) marker 10 of the present invention into a biopsy site. As shown, this device 100 comprises a non-tapered tubular barrel 110 having a substantially cylindrical inner wall 112 and a plunger 114 that is advanceable within the barrel 110. A quantity of a solid marker material of this invention is loaded into the barrel 110 of the device 100, the barrel 100 is inserted into the biopsy site, and the plunger 114 is advanced so as to expel the marker material out of the distal end of the barrel 110 and into the biopsy site.

b. Plurality of Beads or Pellets

FIG. 3b shows an example of an detectable marker 10b that comprises a plurality of beads or pellets of approximately 10–1000 microns in diameter. Each bead or pellet may itself be formed of detectable material that is biodegradeable or otherwise clearable from the biopsy site so as to exhibit the desired detectable residence time as described hereabove such as silver chloride or silver nitrate.

Alternatively, each bead or pellet may contain a detectable material in its interior and the outer surface of the bead or pellet may be a skin or encapsulating material that is biodegradeable such as polyactic acid, so as to provide for the desired detectable residence time within the biopsy site.

Beads or pellets filled with air, carbon dioxide, or other suitable gas may be used as markers 10b of the present invention that are detectable by either ultrasound or x-ray. However, even though such gas-filled markers 10b of the present invention are visible on x-ray, they will not obscure or block x-ray imaging of tissue adjacent to the biopsy cavity and, thus, need not biodegrade or clear from the biopsy site by the second time point (e.g., 5–7 months).

c. Inflatable Balloon

FIG. 3c shows an example of a detectable marker 10c that comprises an inflatable balloon. Such inflatable balloon is passed through the introduction cannula and inflated within the biopsy cavity BC formed within the lesion L. The material of the balloon itself may be detectable and biodegradable or otherwise clearable from the biopsy site so as to exhibit the desired detectable residence time as described hereabove. One example of such a material is polyurethane that has been subjected to hydrolysis in situ. Alternatively, the balloon may contain a detectable material and the balloon itself may form a skin or encapsulating material (e.g., polyurethane) that is biodegradeable so as to provide for the desired detectable residence time within the biopsy site.

Balloons filled with air, carbon dioxide, or other suitable gag may be used as markers 10c of the present invention that are detectable by either ultrasound or x-ray. However, even though such gas-filled markers 10c of the present invention are visible on x-ray, they will not obscure or block x-ray imaging of tissue adjacent to the biopsy cavity and, thus, need not biodegrade or clear from the biopsy site by the second time point (e.g., 5–7 months).

vii. Optional Adhesive For Attaching the Marker to Tissue Adjacent the Site

In any of the above-described embodiments of the invention, the marker 10 may have inherent adhesive properties, or the marker may further comprise an adhesive such as a polyurethane, polyacrylic compound, polyhydroxymethacrylate, fibrin glue (e.g., Tisseal™), collagen adhesive, or other biological or biocompatible adhesive that will cause the marker to adhere to tissue adjacent the biopsy cavity BC. Such optional adhesive will further ensure that the marker 10 does not migrate or move from the biopsy site as tissue surrounding the site is moved, flexed, compressed or decompressed.

B. Method for Surgical Excision of Tissue Located Within a Specific Distance of and/or Adjacent a Specific Location on the Boundary of a Biopsy Site FIGS. 5a–5c show a preferred method for using a visually discernible marker 10 of the present invention to guide the excision and removal of tissues located within a specific band, region or location adjacent the boundaries of the biopsy cavity. As shown in FIG. 5a, a visible marker 10 has been introduced into the biopsy cavity BC so as to permit visualization of the boundary BOU of the biopsy cavity BC by the surgeon. Such visualization of the boundary BOU of this biopsy cavity BC can enable the surgeon to selectively remove tissue that is located within a general zone $Z_1$ of potentially cancerous tissue surrounding the entire biopsy cavity BC (FIG. 5b) or within a specific zone $Z_2$ located on only one side of the biopsy cavity BC (FIG. 5c).

With specific reference to the showing of FIG. 5b, the removal of all tissue within a general zone $Z_1$ surrounding the entire biopsy cavity BC may be desirable in cases where the pathology report has indicated that the previously removed biopsy specimen, had no clear margin and, thus, it is desirable to remove all tissue within the zone $Z_1$ of width X surrounding the biopsy cavity BC on all sides.

With specific reference to the showing of FIG. 5c, the removal of certain tissue within a specific zone $Z_2$ located to one side of an axis that has been projected throughout the biopsy cavity BC may be desirable in cases where the pathology report has indicated that the previously removed biopsy specimen had clear margins on all but one side and, thus, it is desirable to remove only tissue that is located within the specific zone $Z_1$ of width X on one side of the biopsy cavity BC.

The invention has been described hereabove with reference to certain presently preferred embodiments, and no attempt has been made to describe all possible embodiments in which the invention may take physical form. Indeed, numerous modifications, additions, deletions and alterations may be made to the above-described embodiments without departing from the intended spirit and scope of the invention. Accordingly, it is intended that all such additions, deletions, modifications and alterations be included within the scope of the following claims.

What is claimed is:

1. A marker for marking a cavity site within the body of a mammalian patient from which a tissue sample has been removed, said marker formed at least in part of a clearance delaying component, and being characterized by remaining present at the cavity site in sufficient quantity to permit detection and location of the cavity site for at least a predetermined first time period after introduction to the cavity site.

2. An intracorporeal marker for marking a cavity site within the body of a mammalian patient from which A tissue sample has been removed, comprising a mass of material that is detectable by at least two remote imaging detection methods when introduced into the cavity site from which tissue has been removed, that remains detectable at the cavity site for at least a predetermined first time period after its introduction into the cavity site and that does not interfere worth imaging of tissue adjacent the cavity site during a predetermined second period of time after the first period of time.

3. The marker of claim 2 wherein the detectable mass is imageable, and remains imageable for at least the first predetermined time period but clears sufficiently from the site so as to not interfere with imaging of tissue adjacent the site during the second predetermined time period.

4. The marker of claim 3 wherein the detectable mass is imageable by at least one of methods consisting of
    X-ray;
    fluoroscopy;
    mammography;
    computed tomography;
    magnetic resonance imaging;
    ultrasound;
    Doppler,
    radiation detector; and,
    combinations thereof.

5. The marker of claim 2 wherein the detectable mass is detectable by palpation.

6. The marker of claim 5 wherein the detectable mass is selected from the group consisting of:
    at least one balloon;
    at least one bead;
    a viscous, flowable material;
    a collagenous material,
    a gelatinous material;
    cross-linked gelatin; and,
    possible combinations thereof.

7. The marker of claim 2 wherein the detectable mass is visually detectable.

8. The marker of claim 7 wherein the detectable mass includes a colored substance selected from the group consisting of:
    a dye;
    a colorant;
    colorant particles;
    carbon; and,
    possible combinations thereof.

9. The marker of claim 2 wherein the detectable mass is detectable by at least two remote imaging detection methods selected from the group consisting of:
    magnetic resonance imaging (MRI);
    ultrasound imaging;
    Doppler imaging;
    x-ray imaging;
    computer-assisted tomography (CAT);
    mammography;
    fluoroscopy;
    other roentgenological imaging methods;
    visualization; and
    detection of emission.

10. The marker of claim 2 wherein the detectable mass will interfere with imaging of tissue adjacent to the site and will remain at the site in sufficient quantity to permit location of the site by imaging through the first period of time and will clear sufficiently from the site so as to not interfere with imaging of tissue adjacent the site during the second period of time.

11. The marker of claim 2 wherein the detectable mass of material is of sufficient quantity that, if introduced into the cavity site alone, would clear from the cavity site and be not detectable 2 weeks after introduction and includes a clearance delaying component that delays the clearance of said material from the cavity site such that (i) a detectable quantity of said material remains present at the cavity site until at least said first time point and (ii) said material clears sufficiently from the cavity site to permit imaging of tissue adjacent to the cavity site without interference from said detectable marker at said second time point.

12. The marker of claim 11 wherein the detectable mass of material is a chemical compound having a solubility constant of less than $1 \times 10^{-3}$ grams per 100 cubic centimeters of water.

13. The marker of claim 12 wherein said chemical compound is selected from the group consisting of:
    AgCl;
    AgI;
    $BaCO_3$;
    $BaSO_4$;
    K;
    $CaCO_3$;
    ZnO;
    $Al_2O_3$; and,
    the possible combinations thereof.

14. The marker of claim 11 wherein the detectable mass of material is selected from the group consisting of:
    AGNO3;
    ammonium salts;
    sodium salts;
    potassium salts;
    ethiodized oil;
    sohexol;
    isopamidol;
    gas;
    lipid;
    oil; and,
    the possible combinations thereof.

15. The marker of claim 11 wherein the clearance delaying element is selected from the group consisting of:

polylactic acid;
polyglycolic acid;
polycapriolactone;
an encapsulating material;
collagen
renatured collagen;
gelatin;
renatured gelatin;
crosslinked gelatin;
a balloon;
a microsphere; and
the possible combinations thereof.

16. The marker of claim 11 wherein the detectable mass of material is detectable by radiographic imaging.

17. The marker of claim 11 wherein the detectable mass of material is detectable by monographic imaging.

18. The marker of claim 11 wherein the detectable mass of material is detectable by magnetic imaging.

19. The marker of claim 11 wherein the detectable mass of material comprises a dry powder.

20. The marker of claim 11 wherein the detectable mass of material comprises at least one sponge.

21. The marker of claim 11 wherein the detectable mass comprises a suspension.

22. The marker of claim 11 wherein the detectable mass comprises a slurry.

23. The marker of claim 11 wherein the detectable mass comprises a collagenous material having radiographically imageable matter attached thereto.

24. The marker of claim 23 wherein the collagenous material of the marker comprises renatured collagen.

25. The marker of claim 24 wherein the colagenous material is covalently crosslinked.

26. The marker of claim 24 wherein the radiographically imageable matter includes metal ions.

27. The marker of claim 24 wherein the radiographically imageable matter comprises a gas.

28. The marker of claim 24 wherein the collagenous material of the marker comprises renatured collagen and the radiographically imageable matter of the marker comprises metal ions that are bound to said renatured collagen.

29. The marker of claim 28 wherein the metal ions are silver ions.

30. The marker of claim 24 wherein the detectable mass is a gelatinous material having radiographically imageable matter combined therewith.

31. The marker of claim 30 wherein the gelatinous material is renatured gelatin.

32. The marker of claim 30 wherein the gelatinous material is covalently crosslinked.

33. The marker of claim 30 wherein the radiographically imageable matter comprises metal ions.

34. The marker of claim 30 wherein the radiographically imageable matter comprises a gas.

35. The marker of claim 30 wherein the gelatinous material is renatured gelatin and the radiographically imageable matter comprises metal ions that are bound to said renatured gelatin.

36. The marker of claim 35 wherein the metal ions are silver ions.

* * * * *